United States Patent [19]

Riess et al.

[11] 3,983,179
[45] Sept. 28, 1976

[54] 1,2,3,4 TETRAKIS-(PERFLUOROALKYL)-1,3-BUTADIENES

[75] Inventors: Jean Riess; Georges Santini; Maurice Le Blanc, all of Nice, France

[73] Assignee: Produits Chimiques Ugine Kuhlmann, Paris, France

[22] Filed: Jan. 28, 1975

[21] Appl. No.: 544,817

[30] Foreign Application Priority Data
Feb. 12, 1974 France .............................. 74.04599

[52] U.S. Cl. ...................... 260/653.3; 260/653.1 T; 260/653.1 R; 424/351
[51] Int. Cl.² ......................................... C07C 21/20
[58] Field of Search ................. 260/653.3, 653.1 T, 260/653.1 R

[56] References Cited
UNITED STATES PATENTS

| 3,145,222 | 8/1964 | Brace ........................... 260/653.1 T |
| 3,218,303 | 11/1965 | Anderson et al ............. 260/653.1 R |
| 3,317,618 | 5/1967 | Haszeldine ..................... 260/653.3 |

OTHER PUBLICATIONS
Leedham et al., J. Chem. Soc. 1954, pp. 1634–1638.

*Primary Examiner*—D. Horwitz
*Attorney, Agent, or Firm*—Pennie & Edmonds

[57] ABSTRACT

A polyfluorinated butadiene having the formula

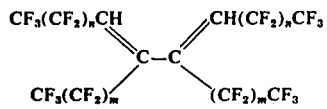

wherein $n$ and $m$ are integers from 1 to 10 and $n=m$ or $n \neq m$, is prepared by reductive coupling, exemplarily with copper, of the corresponding 1,2-bis(perfluoroalkyl)iodoethylene having the formula $CF_3(CF_2)_nCH = CI—(CF_2)_mCF_3$. This iodoethylene is conveniently prepared by a simple addition reaction between a perfluoroalkyl iodide and a perfluoroalkyl acetylene. The perfluoralkylated butadienes are useful as transporters of dissolved gas, particularly of oxygen as in blood substitutes.

7 Claims, No Drawings

1,2,3,4 TETRAKIS-(PERFLUOROALKYL)-1,3-BUTADIENES

BACKGROUND OF THE INVENTION

This invention relates to butadienes substituted on each of their four carbon atoms by a $C_1$-$C_{10}$ perfluoroalkyl group. These novel tetrakis(perfluoroalkyl)-butadienes have utility as transporters of dissolved gas, in particular of oxygen and carbon dioxide. This property makes them especially useful as new substitutes for red blood corpuscles in a physiological technology illustrated by H. A. Sloviter and T. Kamimoto (Nature 216 458 (1967)) and R. P. Geyer (Federation Proceedings 27 952 (1968)) who have prepared emulsions of oxygen-dissolving fluorinated compounds in aqueous physiological saline solution which can be partially or completely exchanged for the blood of mice and dogs.

Fluorinated butadienes are known having the structure $CX_2=CX-CX=CX_2$ where X is hydrogen or halogen. See R. A. Mitsch and E. W. Neuvar, J. Phys.Chem. 70 (2) 546–553 (1966) also G. Camaggi et al, Tetrahedron 22 (6) 1755–63 (1966).

As to perfluoroalkyl butadienes, mono-substituted derivatives having just one perfluoroalkyl group are described in French Pat. Nos. 1,361,255 and 1,361,256, also in U.S. Pat. Nos. 2,945,896 and 2,490,753. Also, bis-perfluoroalkyl butadienes are disclosed in U.S. Pat. No. 3,035,034 and by M. H. Kaufman, J. Polymer-Sci., AI 10 (1971) 455–464 and by P. Tarrant J. Org. Chem. 24 (1959) 1888 and 25 (1960) 2254.

However, to the best knowledge of present applicants, tris and tetrakis(perfluoroalkyl)butadienes have not been specifically described with the exception of fluorinated cyclic products typified by perfluorobicyclo-1, 1'-pentenyl as reported by Camaggi in J. Chem. Soc. (C) (1971) 2382 and Tetrahedron 22 (1966) 1758. Indeed, British Pat. No. 774,103 recites a generalized formula (FIG. 7 on page 7 thereof)

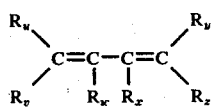

wherein the symbols $R_u$ to $R_z$ are stated to be "appropriately selected to represent hydrogen, halogen, alkyl and halogenoalkyl groups". But a careful reading of this patent reveals no description of any compound having as in the present application $R_u = R_y = H$ and $R_v$, $R_w$, $R_x$, and $R_z$ all equal to $C_1$-$C_{10}$ perfluoroalkyl groups. In fact, no preparations are described which would give an art-skilled person any confidence that the synthetic method of that patent could be adapted to prepare tetrakis-(perfluoroalkyl) products satisfactorily and in good yield. Also the specialized gas-transporting properties of the compounds of the instant invention are not recognized by the British patent.

The method of forming halogenated dienes according to British Pat. No. 774,103, involves a cumbersome succession of steps including the intermolecular deiodination of a saturated compound having a chlorine on the same carbon as the iodine and either hydrogen or chlorine on the carbon adjacent thereto, followed by either dehydrochlorination of dechlorination, as the case may be, to form the desired twofold unsaturation.

Thus, if such a method were attempted to form the compounds of the instant invention, it would be necessary to have as starting materials saturated iodides of the formula

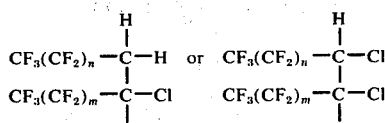

wherein $n$ and $m$ have the same meaning as above described.

Reductive coupling of such compounds would then lead to fully saturated products which would subsequently have to be dehydrochlorinated or dechlorinated respectively to yield the desired dienes. The magnitude of the yields to be expected are of course, unknown - but even if acceptable yields could be obtained the plurality of steps required would be burdensome and costly.

SUMMARY OF THE INVENTION

A simple means has now been found for preparing 1,2,3,4-tetrakis (perfluoroalkyl)-1,3-butadienes.

Briefly stated, the method of this invention comprises reacting a 1,2-bis(perfluoroalkyl)iodoethylene having the formula $CF_3(CF_2)_nCH=CI-(CF_2)_mCF_3$, in the presence of at least a stoichiometric amount of, exemplarily, copper as reducing agent to form the corresponding 1,2,3,4-tetrakis(perfluoroalkyl)-1,3-butadiene having the formula

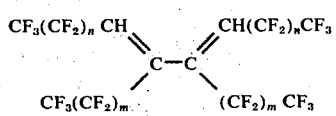

wherein $n$ and $m$ in both formulas are integers from 1 to 10 and $n=m$ or $n \neq m$.

In a preferred embodiment of this method, the 1-iodo-1,2-bis(perfluoroalkyl)ethylene is prepared by reacting a perfluoroalkyliodide and a perfluoroalkyl acetylene.

This invention also relates to the tetrakis perfluoroalkyl butadienes themselves as new products. As discussed above, these products, to the best knowledge of present inventors have not been specifically described in the prior art, nor have their potentialities as carriers of oxygen been recognized or contemplated.

DETAILED DESCRIPTION

The reaction of this invention whereby two molecules of a 1-iodo-1,2 bis(perfluoroalkyl)ethylene are "dimerized" to form the corresponding 1,2,3,4-tetrakis(perfluoroalkyl)-1,3 butadiene is a form of reductive coupling wherein the starting iodo-compound is reduced according to the partial equation

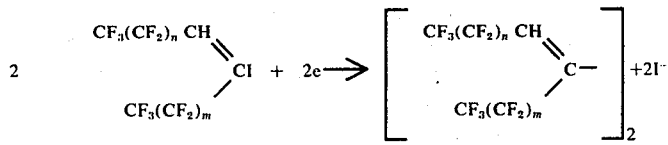

The necessary electrons are supplied by the metallic copper present, which thus acts as a reducing agent according to the second partial equation $$2Cu° \rightarrow 2Cu^+ + 2e$$

The overall stoichiometric reaction is thus substantially between one mol of the starting iodo-compound and one gram atom of metallic copper to form one mol of cuprous iodide CuI and a half mol of the tetrakis(perfluoroalkyl)butadiene. It is of course possible that some of the reducing copper may react further to form cupric $Cu^{++}$ ions, particularly when the copper is not present in excess, whereby some cupric iodide $CuI_2$ may be formed in the reaction. At least a 1:1 stoichiometric amount of copper should be used, i.e. at least one gram atom of copper should be used per mol of starting iodo-compound. In general, in order to expedite the reaction, it is preferred that the copper be in a finely-divided pulverulent form and in excess of stoichiometric amount, such as, for example, at least 2 gram-atoms of copper per mol of starting iodo-compound.

The reductive coupling reaction of this invention is carried out by making a slurry of the copper powder in the 1,2-bis-(perfluoroalkyl)iodoethylene, in the stated ratio, and carrying out the reaction in a closed vessel such as a stirred autoclave or agitated sealed tube, exemplarily of glass or silica, at a convenient temperature and time. Temperatures between 200° and 250°C. are particularly suitable, the time required for reaction being from about 18 to 48 hours.

The perfluoroalkyl groups which can be substituted in the iodoethylene and correspondingly in the product coupled therefrom in the method of this invention can be any alkyl group having from 2 to 100 carbon atoms and having substantially all of its hydrogens replaced by fluorine. Exemplarily, said alkyl groups can be, pentafluoroethyl ($C_2F_5$), heptafluoropropyl ($C_3F_7$), nonafluorobutyl ($C_4F_9$), undecafluoroamyl ($C_5F_{11}$), tridecafluorohexyl ($C_6F_{13}$), pentadecafluoroheptyl ($C_7F_{15}$), heptadecafluorooctyl ($C_8F_{17}$), nonadecafluorononyl ($C_9F_{19}$), perfluorodecyl ($C_{10}F_{21}$), and perfluoroundecyl ($C_{11}F_{23}$). While straight chain alkyl groups are preferred, the perfluorinated alkyl groups can also be branched or individually cyclic. Thus, for example, a butyl group can be normal butyl, isobutyl, secondary butyl or tertiary butyl, octyl can be normal octyl or 2-ethylhexyl, and the perfluorinated alkyl can be undecafluorocyclohexyl.

The 1,2-bis(perfluoroalkyl)ethylenes used in carrying out the method of this invention can be prepared in greater than 80% yield by the reaction of a perfluoroalkyl acetylene with an excess of a perfluoroalkyl iodide. Thus

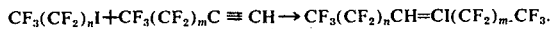

It is preferred to use at least about two mols of the iodide per mol of the substituted acetylene and to confine the reactants in a closed vessel such as a stirred autoclave or an agitated sealed tube suitably of glass or silica. Time of reaction required to reach good yields will depend on the temperature used. Thus, if a temperature between about 200° and 250° C. is used, a reaction time of about 3 to 4 hours will prove sufficient.

The tetrakis(perfluoroalkyl)butadienes of this invention are liquid over a wide range of temperature, usually over more than 250 Centigrade degrees. They have very low vapor pressures. Thus, for example 1,4-bis(perfluorobutyl)-2, 3-bis(perfluorohexyl)-1, 3-butadiene is liquid at ordinary room temperatures, boils at 270°C. and has a vapor tension of only 0.1 mm of mercury at 100°C.

As aforementioned, the tetrakis(perfluoroalkyl) butadienes of this invention are particularly efficacious as substrates for sorbing and transporting gases. Exemplarily, 100 ml. of 1,4-bis(perfluorobutyl)-2,3-bis(perfluorohexyl)-1,3-butadiene dissolves 38 ml. of oxygen or 168 ml. of carbon dioxide at 37°C. under a pressure of 760 torrs.

This invention will be further illustrated by description in connection with the following specific examples of the practice of it wherein, as also elsewhere herein, proportions are by weight unless stated otherwise.

EXAMPLE 1

A mixture of 34.4 grams of perfluorohexyl acetylene (0.1 mol) and 89.2 grams of 1-iodoperfluorohexane (0.2 mol) is heated for a period of 3 hours at 220°C. in a closed vessel. The resulting mixture is washed three times with 10 ml of a 10% aqueous solution of potassium iodide, then fractionally distilled under vacuum. There is successively recovered in an ice trap 42.6 of unreacted 1-iodoperfluorohexane (corresponding to 96% of the excess amount used) boiling at about 25°C. under 12 torrs pressure; also 72.7 grams of 1,2-bis(perfluorohexyl)iodoethylene $C_6F_{13}$ CH =CI$C_6F_{13}$ (corresponding to a yield of 92%) boiling at 81°C. under 12 torrs pressure; also 1. 1 gram of 1-iodo-1,3,4-tris(perfluorohexyl)-1,3 butadiene corresponding to the formula

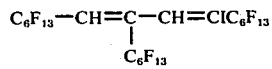

and boiling at 90°C. under 0.2 torrs pressure. The undistilled residue (3.1 grams) is also identified as this last compound. This telomer thus comprises 7% of the total products.

The 1,2-bis(perfluorohexyl)iodoethylene has been identified by means of proton and fluorine nuclear magnetic resonance (NMR), by mass spectrometry and by quantitative chemical elemental analysis.

To 39.50 grams of (0.05 mol) of 1,2-bis(perfluorohexyl)-iodoethylene retained from the first part of this example, there is then added 6.5 grams of powdered copper (0.102 gram-atoms) and the mixture is heated for 24 hours at 220°C. in a closed vessel. After cooling, the obtained pasty mixture is taken up in 50 ml. of trichlorotrifluoroethane (FORANE 113) and filtered under vacuum. The beige-rose precipitate of copper and cuprous iodide is washed three times by 10 ml. of trichlorotrifluoroethane.

After evaporation of the solvent and distillation under reduced pressure, fractions are recovered comprising, in mol percent of starting $C_6F_{13}$ CI = $CHC_6F_{13}$,

| | |
|---|---|
| 10% of | $C_6F_{13}CH = CH_2CF_{13}$ |
| 2% of | $C_6F_{13}CI = CHC_6F_{13}$, |
| and 72% of | 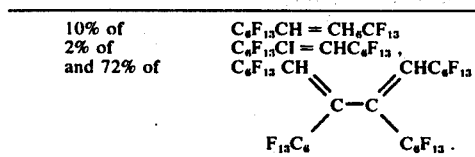 |

The last product has been identified by elemental analysis, by infra-red (IR) spectrometry, by proton and fluorine NMR and by mass spectrometry.

EXAMPLES 2 to 5

By operating in a manner identical to that described in Example 1, using 0.2 mol of $R_FI$ and 0.1 mol of $R_F'$ C = CH and about 0.1 gramatomic weight of copper per 0.05 mol of $R_FCH = CIR_F'$, the results obtained are as summarized in the accompanying Table I.

The product of Example 2 was 1,4-bis(perfluorohexyl)-2,3-bis(perfluorooctyl)-1,3 butadiene and was prepared by coupling 1-iodo-1-perfluorooctyl-2-perfluorohexylethylene which was made by reacting perfluorohexyl iodide with perfluorooctyl-acetylene; the product of Example 3 was 1,2,3,4 tetrakis(perfluorooctyl)-1,3-butadiene and was prepared by coupling 1-iodo-1,2 di(perfluorooctyl) ethylene which was made by reacting perfluorooctyliodide with perfluorooctyl acetylene; the product of Example 4 was 1,4-bis(perfluorobutyl)-2,3-bis-(perfluorooctyl)-1,3-butadiene and was prepared by coupling 1-iodo-1-perfluorooctyl-2-perfluorobutylethylene which was made by reacting perfluorobutyl iodide with perfluorooctyl acetylene; and the product of Example 5 is 1,4-bis(perfluorobutyl)-2,3-bis(perfluorohexyl)-1,3-butadiene and was prepared by coupling 1-iodo-1-perfluorohexyl-2-perfluorobutyl ethylene which was made by reacting perfluorobutyl iodide with perfluorohexyl acetylene. In all cases, the perfluoroalkyl groups were normal straight-chain alkyls.

TABLE I

| | $R_FCH=CIR'_F$ | $R_FCH=CR'_F—CR'_F=CHR_F$ | | |
|---|---|---|---|---|
| | 1,2-Bis-(perfluoroalkyl)-iodo-ethylene Being Coupled | Resulting Product of coupling | Boiling Point °C  mmHg | Yield |
| Ex.1 | $C_6F_{13}CH=CCl-C_6F_{13}$ | $[C_6F_{13}CH=C(C_6F_{13})-]_2$ | 175  12 | 72% |
| Ex.2 | $C_8F_{17}CH=CCl-C_8F_{17}$ | $[C_8F_{17}CH=C(C_8F_{17})-]_2$ | 145  0.03 | 74% |
| Ex.3 | $C_8F_{17}CH=CCl-C_8F_{17}$ | $[C_8F_{17}CH=C(C_8F_{17})-]_2$ | 166  0.03 | 73% |
| Ex.4 | $C_4F_9CH=CCl-C_8F_{17}$ | $[C_4F_9CH=C(C_8F_{17})-]_2$ | 130  0.03 | 62% |
| Ex.5 | $C_4F_9CH=CCl-C_6F_{13}$ | $[C_4F_9CH=C(C_6F_{13})-]_2$ | 100  0.1 | 77% |

We claim:

1. A 1,2,3,4-tetrakis(perfluoroalkyl)-1,3-butadiene having the formula

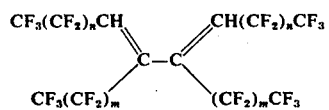

wherein $n$ and $m$ are integers from 1 to 10 and $n = m$ or $n \neq m$.

2. 1,2,3,4-tetrakis(tridecafluorohexyl)-1,3-butadiene.

3. 1,2,3,4-tetrakis(heptadecafluorooctyl)-1,3-butadiene.

4. 1,4-bis(tridecafluorohexyl)-2,3-bis-(heptadecafluorooctyl)-1,3-butadiene.

5. 1,4-bis(nonafluorobutyl)-2,3-bis-(heptadecafluorooctyl)-1,3-butadiene.

6. 1,4-bis(nonafluorobutyl)-2,3-bis-tridecafluorohexyl)1,3-butadiene.

7. A method for preparing a 1,2,3,4-tetrakis-(perfluoroalkyl)-1,3-butadiene having the formula

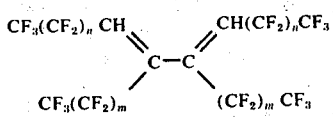

wherein $n$ and $m$ are integers from 1 to 10 and $n=m$ or $n \neq m$, said method comprising reacting a 1,2-bis(perfluoroalkyl)iodoethylene having the formula $CF_3(CF_2)_n-CH=CI-(CF_2)_mCF_3$, in which the values of $n$ and $m$ correspond respectively to those of said tetrakis (perfluoroalkyl) butadiene, in the presence of at least a stoichiometric amount of copper as reducing agent.

* * * * *

UNITED STATES PATENT AND TRADEMARK OFFICE
CERTIFICATE OF CORRECTION

PATENT NO. : 3,983,179
DATED : September 28, 1976
INVENTOR(S) : Jean Riess et al.

It is certified that error appears in the above-identified patent and that said Letters Patent are hereby corrected as shown below:

In the abstract "$n \quad m$" should be --$n \neq m$--

Column 3, line 45 "2 to 100" should be --2 to 11--

Column 5, line 65 "$R'_6$" should be --$R'_F$--

Signed and Sealed this

Seventeenth Day of May 1977

[SEAL]

Attest:

RUTH C. MASON
Attesting Officer

C. MARSHALL DANN
Commissioner of Patents and Trademarks